(12) United States Patent
Mousselon et al.

(10) Patent No.: US 7,146,982 B2
(45) Date of Patent: Dec. 12, 2006

(54) INTRAORAL ORTHOSIS FOR PREVENTING SNORING

(75) Inventors: Philippe Mousselon, Lyons (FR); Ludovic Baratier, Lyons (FR)

(73) Assignee: Laboratories Norval SA (FR)

( * ) Notice: Subject to any disclaimer, the term of this patent is extended or adjusted under 35 U.S.C. 154(b) by 0 days.

(21) Appl. No.: 10/493,680

(22) PCT Filed: Oct. 25, 2002

(86) PCT No.: PCT/FR02/03684

§ 371 (c)(1),
(2), (4) Date: Sep. 16, 2004

(87) PCT Pub. No.: WO03/034957

PCT Pub. Date: May 1, 2003

(65) Prior Publication Data

US 2005/0016547 A1    Jan. 27, 2005

(30) Foreign Application Priority Data

Oct. 26, 2001   (FR) .................................. 01 13918

(51) Int. Cl.
*A61C 5/14*   (2006.01)

(52) U.S. Cl. ........................ 128/848; 433/6; 128/861
(58) Field of Classification Search .................. 433/19, 433/6; 128/861, 859, 848
See application file for complete search history.

(56) References Cited

U.S. PATENT DOCUMENTS

| 5,752,822 A * | 5/1998 | Robson ........................ 433/6 |
| 6,055,986 A * | 5/2000 | Meade ....................... 128/848 |
| 6,302,686 B1 * | 10/2001 | Chott et al. .................... 433/6 |
| 6,418,933 B1 * | 7/2002 | Strong ....................... 128/848 |

* cited by examiner

*Primary Examiner*—Melba Bumgarner
(74) *Attorney, Agent, or Firm*—Cantor Colburn LLP

(57) ABSTRACT

The invention concerns an intraoral orthosis comprising an upper groove (2) and a lower groove (3) designed to line respectively an upper jaw and a lower jaw, said grooves (2, 3) being linked together by two tie rods (4) of such length that the lower jaw is maintained in an extended position relative to the upper jaw. Additionally, a system for fixing the tie rods (4) on the grooves (2, 3) maintains them substantially in the occlusal plane in contact with the upper and lower teeth.

16 Claims, 4 Drawing Sheets

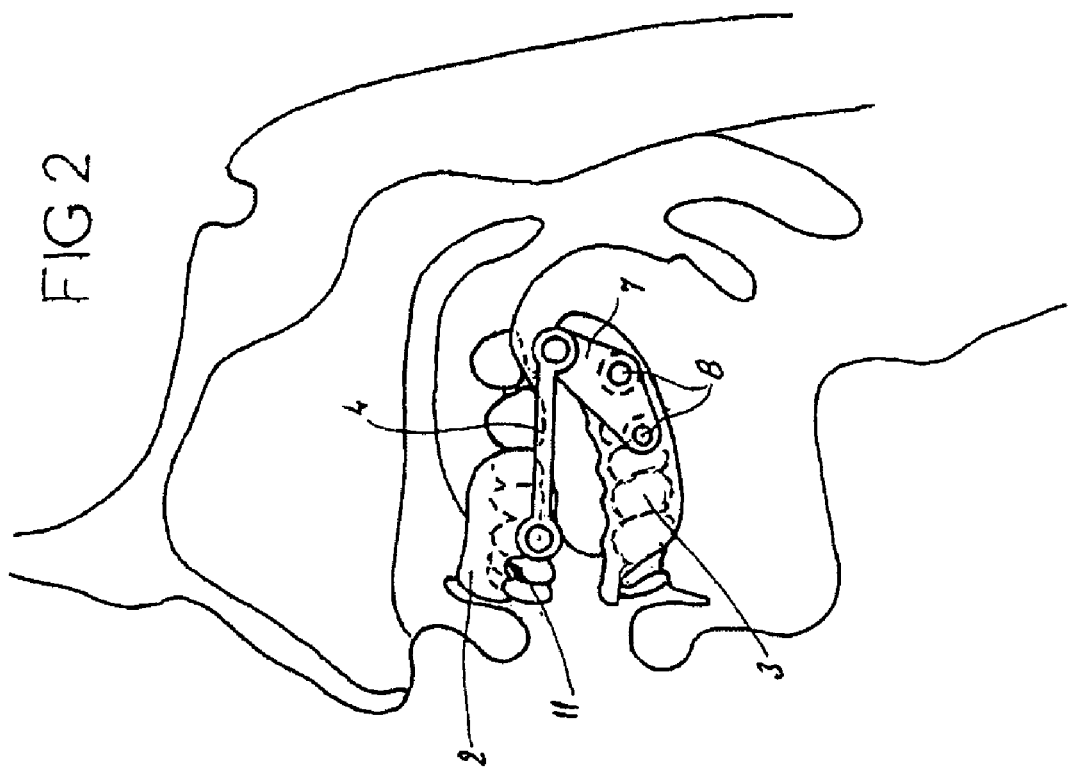
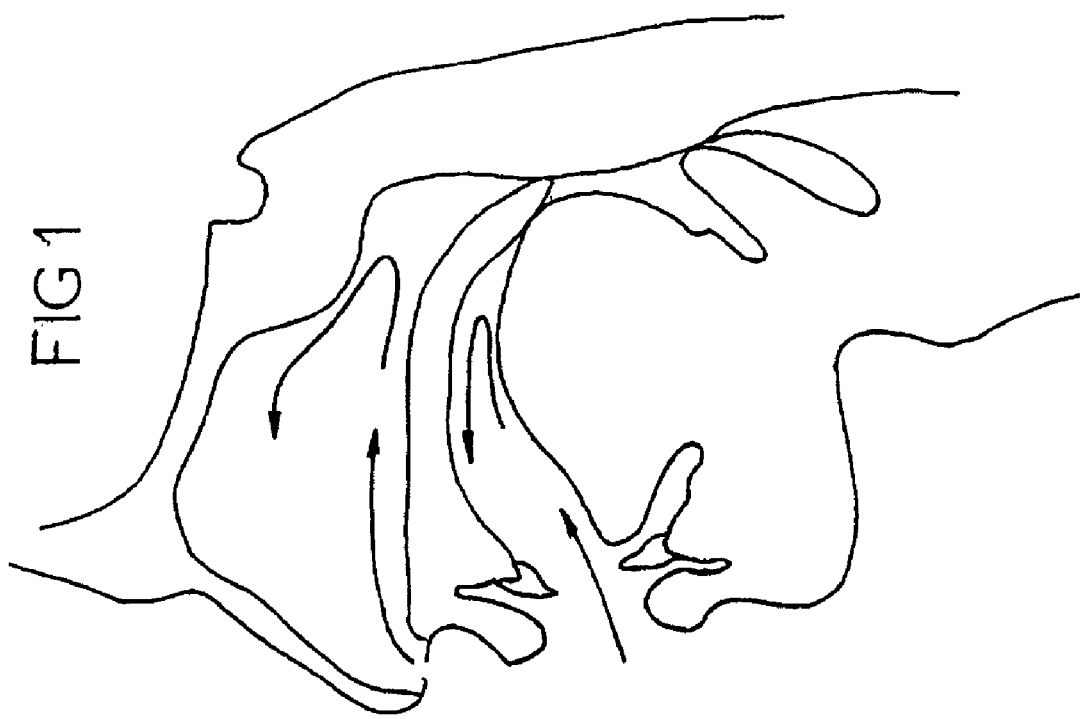

INTRAORAL ORTHOSIS FOR PREVENTING SNORING

The present invention relates to an intraoral orthosis for preventing snoring and obstructive sleep apnea.

Chronic snoring is a condition affecting a considerable proportion of the population, estimated at 40% by some studies.

During sleep, the patient's throat muscles relax, causing a narrowing of the pharynx, as is shown diagrammatically in FIG. 1.

The consequence of this narrowing is an increase in the speed of the inhaled air caused by a venturi-type effect. The air excites the flexible part of the soft palate and uvula and these begin to vibrate noisily. The noise created in this way can reach up to 90 decibels.

In some cases, the narrowing is such that breathing may stop for ten seconds or so, or even longer in some patients.

This phenomenon, called sleep apnea, results in the patient resuming breathing in a sudden and noisy manner.

There are, therefore, a great many devices available for preventing snoring.

One of the most effective is an intraoral orthosis which causes an advancement of the lower jaw. This advancement of the lower jaw permits widening of the pharyngeal zone.

As a result of the disappearance of the narrowing due to relaxation of the muscles, air is inhaled at normal speed and the vibrations of the flexible parts of the soft palate and of the uvula disappear.

Among orthoses of this type, there are some which comprise two thermoformed splints, one of which is intended to fit the teeth of the upper jaw, and the other of which is intended to fit the teeth of the lower jaw.

These two splints are connected laterally by two tie rods.

The tie rods are fixed symmetrically on the upper splint in the area of the canines and on the lower splint in the area of the first molars, the length of the tie rods being such that when the orthosis is placed in a patient's mouth, the lower jaw is held in an advanced position.

The orthoses of this type significantly reduce snoring and are well tolerated by patients. However, they have certain limitations.

In particular, many cases are observed in which the splints come loose when the patient unconsciously opens his mouth during sleep.

As the jaws move away from one another, on account of the splints being connected to one another via the tie rods, the splints come loose from the jaws and the orthosis is expelled from the mouth.

The patient is then no longer being treated and is therefore once again subject to snoring.

Another disadvantage associated with these orthoses lies in the fact that adjusting the length of the tie rods is awkward since it is necessary to disassemble and then completely refit the orthosis with tie rods of different length. However, the length of the tie rods is a critical parameter in this type of orthosis because tie rods that are too long produce insufficient advancement of the lower jaw, while tie rods which have too short a length are not supported by the patient.

It is therefore an object of the invention to make available an intraoral orthosis for preventing snoring which has a better hold on a patient's jaws.

Another object of the invention is to make available an orthosis permitting easy adjustment of the advancement of the lower jaw.

In a manner known per se, the orthosis comprises:
- an upper splint and a lower splint designed to line the teeth of an upper jaw and the teeth of a lower jaw, respectively,
- two tie rods connecting the splints, these tie rods being of such a length that the lower jaw is maintained in an advanced position relative to the upper jaw.

According to the invention, the tie rods have fixed points of attachment to the splints,
- on the one hand, to the upper splint in the area of the canines, and
- on the other hand, to the lower splint in the area of the second mandibular molar, the lower splint comprising means for fixation of the tie rods, making it possible to shift the point of attachment of the tie rods in the occlusal plane of contact of the lower and upper teeth.

The tie rods which exert traction on the lower splint, and hence on the lower jaw, are situated parallel to the auriculo-orbital plane also called the Frankfort plane. By virtue of this arrangement, the traction of the tie rods is effected according to a component virtually parallel to the occlusal plane. The orthosis is thus much less subject to coming loose.

According to a preferred embodiment, the lower splint is equipped with attachment brackets comprising a part fixed by two rivets in line with the first and second molars, and a part extending obliquely at about 120° in the direction of the occlusal face of the second molar.

By virtue of this arrangement of the brackets, the point of fixation of each of the tie rods on the lower splint is offset in a posterior position, permitting the use of tie rods of greater length. These tie rods, whose length is maximized, give the orthosis a very good hold on the jaws, particularly if the mouth is opened.

The upper splint advantageously extends on an arc whose ends stop in the area of the distal face of the second maxillary premolars.

By virtue of this arrangement, the upper splint not covering the molars is less intrusive than the known splints. This cutting prevents premature contact of the maxillary and mandibular splints at the occlusal faces of the molars.

Moreover, the splints each have, in their wall, a cutting in the area of the incisors.

In one advantageous possibility, a ball and socket joint provides for the connection between the tie rods and the splints.

According to an alternative embodiment, the tie rods have means permitting adjustment of their length.

For easy adjustment, the tie rods have two threaded holes into which a rod is screwed, the ends of which rod have an inverse pitch, with a nut being placed at the middle of the rod.

By acting on the rod, it is possible to lengthen or shorten the tie rods without having to dismantle them from the orthosis.

According to one embodiment, the tie rods comprise a cylindrical cavity in which there slides, under the action of a hydraulic pressure, a rod whose end comprises a piston.

In addition, the piston delimits two chambers which are each connected via a flexible conduit to two actuators.

By acting on one or other of the actuators, it is possible to act on the orthosis when the latter is positioned in a patient's mouth, in order to determine the optimal length of the tie rods.

According to another possibility, the tie rods comprise two small bars sliding one inside the other, each being provided with bores.

To ensure that the invention is clearly understood, it is described with reference to the drawing which shows, by way of a non-limiting example, an intraoral orthosis according to the invention.

FIG. 1 is a diagrammatic representation of a sagittal section through the nasal cavity, the oral cavity and the region of the pharynx of a patient who snores.

FIGS. 2 and 3 are side views of an orthosis positioned on the lower and upper jaws.

Figure 3:
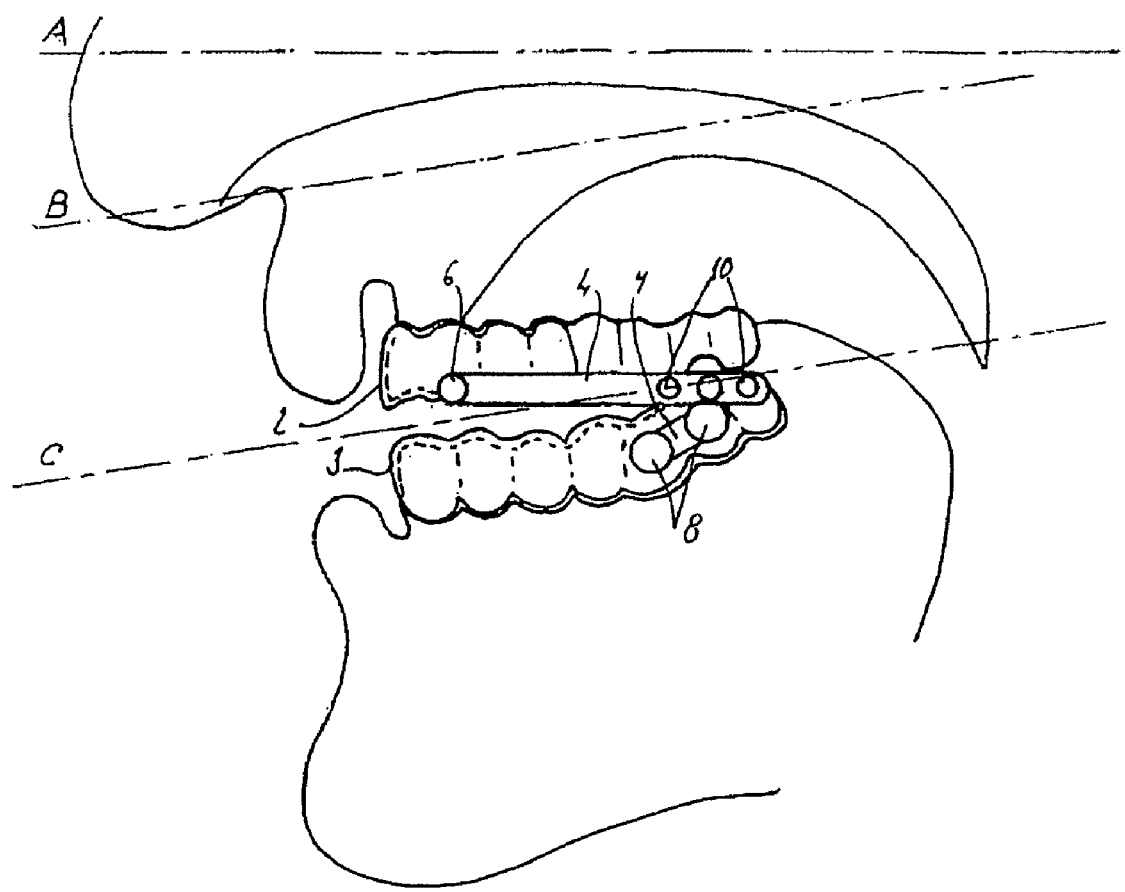
Figure 4:
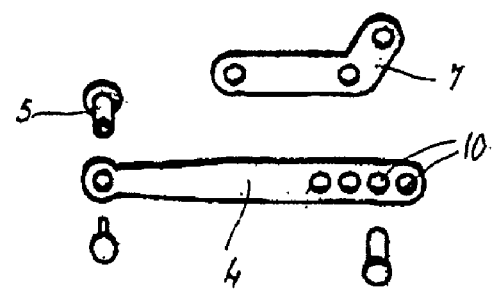
FIG. 4 is an exploded perspective view of the means for fixing a tie rod of this orthosis.

Referring to FIGS. 2 and 3, it will be seen that the orthosis intended to be fitted in the mouth of a patient comprises an upper splint 2 and a lower splint 3 which are connected by two tie rods 4.

The planes labeled A, B, C show the Frankfort plane, Camper plane and occlusal plane, respectively.

The splints 2, 3 are produced by thermoforming according to the morphological characteristics of the jaws of the patient so that they fit these exactly.

According to one possibility, the thermoforming material may consist of two co-extruded materials, one hard layer and one flexible layer, affording good comfort and having a suction effect which contributes to the good hold of the splints.

In the area of forward dental members, such as in an area of each of the canines, the upper splint 2 has a pivot connection formed by a rivet 5 with the upper end of each of the tie rods 4.

The lower splint 3 is equipped with two brackets 7 having a free end on which the lower end of each of the tie rods 4 is articulated.

Each of the brackets 7 comprises a part retained on the lower splint 3 by two rivets 8, these rivets 8 being arranged opposite first and second dental members, such as opposite to the first and second molars, and a part extending obliquely at about 120° in the direction of the occlusal face of this splint. This angle of 120° allows the end of the bracket 7 to be located in the area of the occlusal face of a rear dental member, such as the second mandibular molar.

The tie rods 4 are thus articulated by a pivot connection on the upper splint 2 and by a pivot connection on the end of the bracket 7.

Moreover, the end of the tie rods 4 situated toward the lower splint 3 is drilled with four holes 10 making it possible to adjust the length of these tie rods.

As can be seen from FIG. 2, the upper splint 2 covers an oral part, namely the jaw, in an arc which ends in the area of the distal face of a lower rear dental member, such as the second premolars.

A patient who snores is invited to fit the orthosis in place, the splints 2, 3 fitting over upper and lower oral parts, namely the upper and lower jaws, respectively.

The tie rods 4, which exert a traction on the lower splint 3 and thus on the lower jaw, are situated parallel to the Frankfort plane, and virtually in the plane of contact of the lower and upper dental members (-teeth).

The positioning of the tie rods 4 in this plane is made possible by the fact that the lower end of the tie rods 4 is fixed on a raised point above the occlusal face of the splints.

By virtue of this arrangement, the traction of the tie rods 4 is effected according to a component parallel to the Frankfort plane.

The limitation of the component of vertical traction affords a very good hold of the splints 2, 3 since traction according to too great a vertical component entails a considerable risk of loosening of the splints 2, 3.

In addition, the offset of the lower point of articulation of the tie rods 4 in the area of the second molar permits use of tie rods 4 having a maximized length so that when the patient opens his mouth during sleep, the tie rods 4 orient themselves in a direction whose horizontal component remains very much greater than the vertical component.

There is therefore no loosening of the splints.

In addition, it should be noted that the upper splint 2 which does not cover the molars is much less intrusive than the known splints. This cutting avoids premature contact of the splints in the area of the occlusal faces of maxillary and mandibular dental members, namely the maxillary and mandibular molars.

It will also be noted that the splints can have cuttings 11 in the area of forward dental members, namely the central and lateral incisors, with the aim of forming an orthosis which is as non-intrusive as possible.

Figure 5:
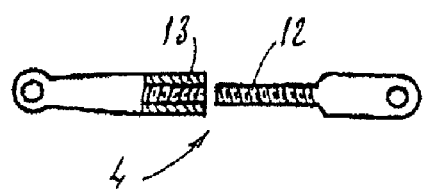
FIGS. 5 to 7 show alternative embodiments of this tie rod.
Figure 6:
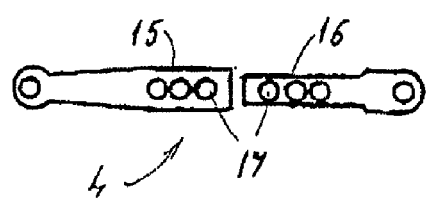
Figure 7:
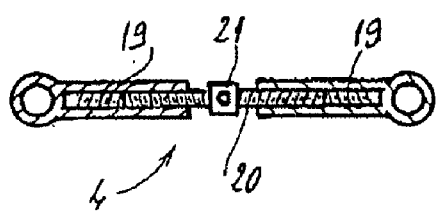

FIGS. 5 to 7 show embodiments of the tie rods 4 permitting simple adjustment of their length.

The tie rod shown in FIG. 5 comprises two elements, one of which has a threaded rod 12, and the other of which has a threaded bore 13 intended to receive the rod 12.

By screwing or unscrewing one of the elements relative to the other, the patient is able to act on the length of the tie rod 4 and adjust it as a function of his snoring or tolerance.

FIG. 6 shows another possible embodiment of the tie rods 4, where the tie rods 4 comprise two small bars 15, 16 which slide one inside the other and are provided with holes 17 making it possible to adjust the length of the tie rods 4.

In FIG. 7, it will be seen that the tie rods 4 have two threaded bores 19 into which is screwed a rod 20 whose ends have an inverse pitch. A nut 21 placed at the middle of the rod 20 allows the latter to be turned in order to lengthen or shorten the tie rods 4 without having to dismantle the tie rods 4 from the orthosis.

Figure 8:
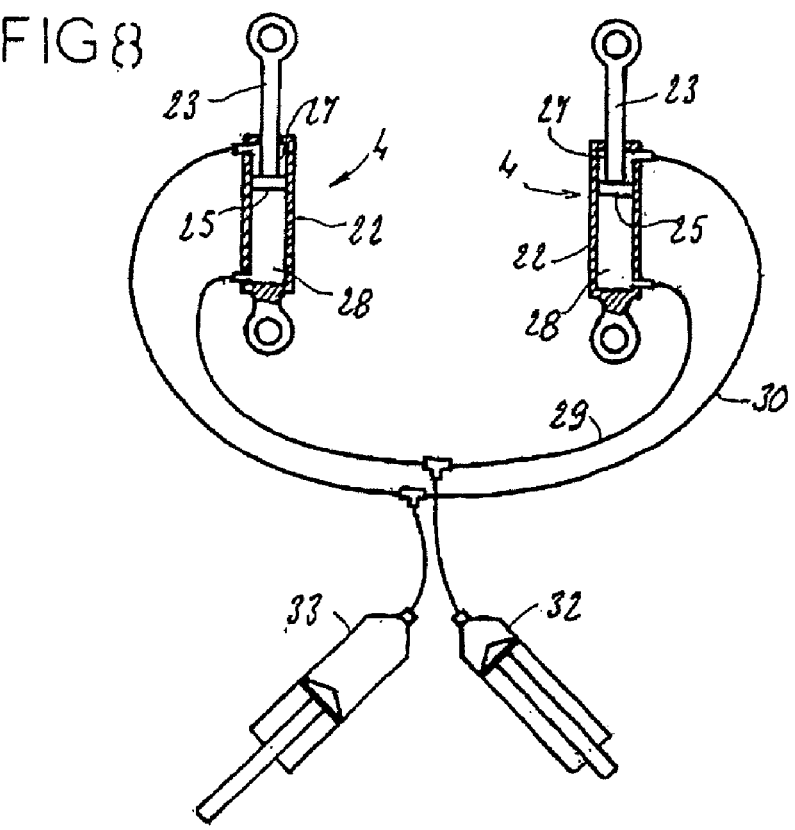
FIG. 8 shows an embodiment of an adjustable tie rod.

FIG. 8 shows an alternative embodiment of the orthosis adapted for clinical examination with a view to determining the optimal length of the tie rods 4.

As can be seen in cross section in this figure, the tie rods 4 each comprise a cylinder 22 in which a rod 23 slides.

The free end of the rod 23 is equipped with a piston 25 which delimits two chambers 27, 28, each connected via flexible conduits 29, 30 to a device with which it is possible to exert a hydraulic pressure on the piston 25.

In the example shown, these devices consist of actuators 32 with which it is possible to exert a pressure in one or other of the chambers 27, 28 and, consequently, to displace the rod 23 of each of the tie rods 4 and hence lengthen or shorten the length of these.

In some cases, patients with particularly severe snoring are hospitalized and their sleep parameters are analyzed.

The orthosis is thus placed in the patient's mouth and the polysomnographic parameters of the patient are recorded.

By acting on one or other of the actuators 32, it is possible to act on the orthosis in situ, and the recordings make it possible to determine the optimal length of the tie rods 4, which may have different lengths depending on the morphology of the patient.

Each of the actuators is in fact connected by a Y-shaped or T-shaped connector piece to the two tie rods, so that there is a balance of the pressures prevailing in the right-hand tie rod and the left-hand tie rod, this balance being a function of the particular forces generated by the neuromuscular system of the patient.

It is thus possible to precisely determine the optimal length of the left-hand and right-hand tie rods during the polysomnographic recording, these tie rods possibly having different lengths since the human body is not symmetrical.

It is also possible to provide a single actuator 33 connected by a Y-shaped or T-shaped connector piece to the chamber 27 of each tie rod 4 so as to act on the traction applied to the mandible. It should be noted that, although this is not shown in FIG. 8, it is possible to alternatively provide for mechanical means such as wires to control the length of the tie rods 4 in order to avoid placing, in the patient's mouth, a hydraulic appliance in which a fluid at high pressure circulates, with risks of escape, the consequences of which would be very damaging to the oral cavity.

Figure 9:
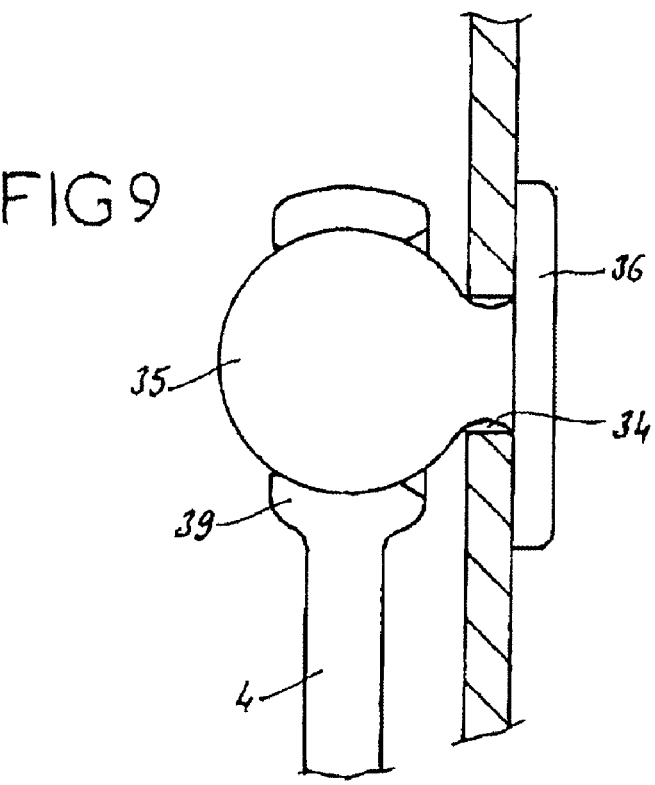
FIGS. 9 and 10 show two embodiments of the connection of the tie rods on the orthosis.
Figure 10:
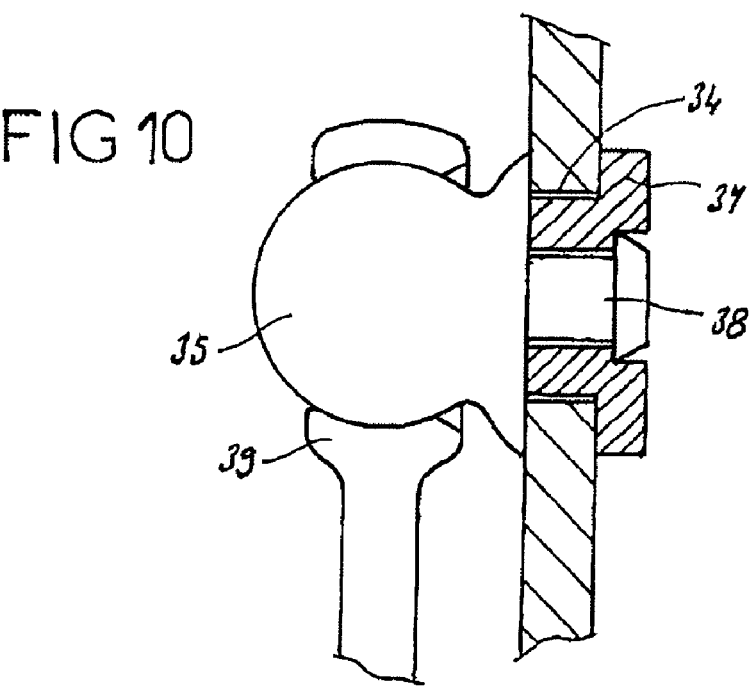

Referring to FIGS. 9 and 10, it will be seen that the tie rods can be articulated on the splints by ball and socket joints. For this purpose, as can be seen from FIG. 9, a hole 34 is drilled in the wall of the splint and a ball 35 is engaged through this, the ball being retained by a disk 36. The connection represented in FIG. 10 uses an insert 37 which is engaged in the hole 34. The ball 35 has a pin 38 which snaps into the insert 37. In these two alternative embodiments, the tie rods have an eye 39 which engages on the ball 35.

The invention thus makes available an intraoral orthosis having the numerous advantages indicated above. This orthosis has an excellent hold on the dental arches by virtue of maximizing the length of the tie rods. In addition, by virtue of its adjustable tie rods, it can be adjusted optimally to the morphology of each patient.

It goes without saying that the invention is not limited to the embodiment described above by way of example, and that instead it encompasses all alternative embodiments thereof. Thus, the length of the tie rods could be adjusted by means of a rack into which a flexible tongue latches. In addition, locking means could be provided on the tie rods shown in FIG. 7, making it possible to fix the length of these in their optimal position which has been determined by experiment. Provision could also be made for the rivets 8 to be interconnected in order, on the one hand, to rigidify the splint and, on the other hand, to obtain a better distribution of the traction forces on the splint supporting the bracket.

The invention claimed is:

1. An intraoral orthosis comprising:
    an upper splint and a lower splint designed to line upper dental members of an upper oral part and lower dental members of a lower oral part, respectively, and
    two tie rods connecting the splints, the tie rods being of such a length that the lower oral part is maintained in an advanced position relative to the upper oral part,
    wherein the tie rods have fixed points of attachment to the upper splint in an area of forward dental members and to the lower splint in an area of a rearward dental member,
    wherein the lower splint comprises attachment brackets fixing the tie rods, making it possible to shift the points of attachment of the tie rods in an occlusal plane of contact of the lower and upper dental members, the attachment brackets comprising a first part fixed to the lower splint and a second part extending obliquely in a direction of the upper splint,
    wherein the first part is fixed by two rivets in line with a first and a second dental member and the second part extends obliquely at about 120° in the direction of an occlusal face of the second dental member.

2. The orthosis as claimed in claim 1, wherein the upper splint extends on an arc having ends stop behind a third dental member.

3. The orthosis as claimed in claim 2, wherein the third dental member is second maxillary premolar.

4. The orthosis as claimed in claim 1, wherein the splints each have, in a wall, a cutting which frees central and lateral dental members.

5. The orthosis as claimed in claim 4, wherein the central dental member is central incisors and the lateral dental member is lateral incisor.

6. The orthosis as claimed in claim 1, wherein a ball and socket joint provides the connection between the tie rods and the splints.

7. The orthosis as claimed in claim 6, wherein the tie rods have two threaded bores, a rod screwed into the bores, wherein ends of the rods have an inverse pitch, and a nut being placed at a middle of the rod.

8. The orthosis as claimed in claim 6, wherein the tie rods comprise a cylinder and a rod having an end comprising a piston, wherein the rod slides in the cylinder under action of a hydraulic pressure.

9. The orthosis as claimed in claim 8, wherein the piston delimits two chambers connected via a flexible conduit to two actuators.

10. The orthosis as claimed in claim 6, wherein the tie rods comprise two small bars sliding relative to each other, the bars comprising bores.

11. The orthosis as claimed in claim 6, wherein a single actuator is connected, via two conduits, to the two tie rods whose length is adjustable as a function of the load applied by the actuator.

12. The orthosis as claimed in claim 1, wherein the tie rods have means permitting adjustment of their length.

13. The orthosis as claimed in claims 1, wherein the splints are made of a two-component material comprising a hard material and a flexible material.

14. The orthosis as claimed in claim 1, wherein the forward dental members are canine teeth.

15. The orthosis as claimed in claim 1, wherein the rearward dental member is a second mandibular molar.

16. The orthosis as claimed in claim 1, wherein the first dental member is a first molar and the second dental member is a second molar.

* * * * *

UNITED STATES PATENT AND TRADEMARK OFFICE
CERTIFICATE OF CORRECTION

PATENT NO. : 7,146,982 B2  Page 1 of 1
APPLICATION NO. : 10/493680
DATED : December 12, 2006
INVENTOR(S) : Mousselon et al.

It is certified that error appears in the above-identified patent and that said Letters Patent is hereby corrected as shown below:

TITLE PAGE

Item (73) Assignee:

Delete "Laboratories Norval SA" and insert therefor --Laboratoires NARVAL SA--.

Signed and Sealed this

Seventeenth Day of November, 2009

David J. Kappos
*Director of the United States Patent and Trademark Office*